United States Patent [19]

Lee et al.

[11] 4,435,422
[45] Mar. 6, 1984

[54] 5-SUBSTITUTED 2,3-DIHYDROBENZOFURAN-2-CARBOXYLIC ACIDS AND THEIR USE IN DIURETIC COMPOSITIONS

[75] Inventors: Cheuk M. Lee, Libertyville; James A. Parks, North Chicago, both of Ill.

[73] Assignee: Abbott Laboratories, North Chicago, Ill.

[21] Appl. No.: 418,321

[22] Filed: Sep. 15, 1982

[51] Int. Cl.³ .................. A61K 31/34; C07D 307/85
[52] U.S. Cl. ................................ 424/285; 549/462; 549/467; 549/468
[58] Field of Search ............... 549/462, 467, 468; 424/285

[56] References Cited

U.S. PATENT DOCUMENTS 4,237,144 12/1980 Cragoe, Jr. et al. ............... 549/468
4,296,122 10/1981 Cragoe, Jr. et al. ............... 549/468

Primary Examiner—Henry R. Jiles
Assistant Examiner—Bernard Dentz
Attorney, Agent, or Firm—Martin L. Katz; Gildo E. Fato

[57] ABSTRACT

Described are compounds of the formula

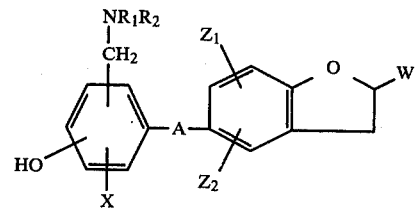

wherein $R_1$ and $R_2$ independently of one another denote hydrogen or loweralkyl; A is CO, $CH_2$, O, S, SO or CHOH; X is hydrogen, halo, loweralkyl, or $-CH_2NR_1R_2$ wherein $R_1$ and $R_2$ are as defined above; W is COOR wherein R is hydrogen or alkyl of 1–10 carbon atoms, $CH_2OH$, $CONR_1R_2$ or $CH_2NR_1R_2$ wherein $R_1$ and $R_2$ are as defined above; $Z_1$ and $Z_2$ independently of one another denote hydrogen, halo or loweralkyl; and pharmaceutically acceptable salts thereof.

The compounds are effective as diuretic agents.

31 Claims, No Drawings

5-SUBSTITUTED 2,3-DIHYDROBENZOFURAN-2-CARBOXYLIC ACIDS AND THEIR USE IN DIURETIC COMPOSITIONS

BACKGROUND OF THE INVENTION

The present invention relates to compounds which are particularly useful in therapeutics as active medicaments for the treatment of hypertension, edema of all types, and other conditions involving fluid and electrolyte accumulation. A diuretic composition in dosage unit form is described.

SUMMARY OF THE INVENTION

The present invention is directed to compounds of the formula

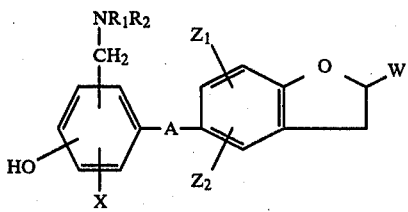

wherein $R_1$ and $R_2$ independently of one another denote hydrogen or loweralkyl; A is CO, $CH_2$, O, S, SO or CHOH; X is hydrogen, halo, loweralkyl, or $-CHN_2R_1R_2$ wherein $R_1$ and $R_2$ are as defined above; W is COOR wherein R is hydrogen or alkyl of 1-10 carbon atoms, $CH_2OH$, $CONR_1R_2$ or $CH_2NR_1R_2$ wherein $R_1$ and $R_2$ are as defined above; $Z_1$ and $Z_2$ independently of one another denote hydrogen, halo or loweralkyl; and pharmaceutically acceptable salts thereof.

The compounds contain an asymmetric carbon atom at the 2- position of the benzofuran ring and therefore the compounds described include racemic mixtures or d and l- isomers.

The term "loweralkyl" as used herein refers to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsilate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For oral administration, amounts of from about 0.1 to 200 mg./kg. per day per patient are useful, with the total dose of up to 1 gm. per day being a suitable range for large animals, including humans. The whole dosage range described increases the total urinary excretion from about 2 to about 10-fold in most animals. From these figures, it is apparent that the new diuretic compounds are particularly effective in increasing urinary excretion in most animals.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

In order to illustrate the manner in which the above compounds may be prepared and the properties of the compounds, reference is made to the following examples, which, however, are not meant to limit or restrict the scope of the invention in any respect.

The phenoxyacetate derivatives of the invention were prepared according to the following reaction scheme. Compounds of the invention other than depicted can be made in the same manner using the appropriate starting materials.

Reaction Scheme

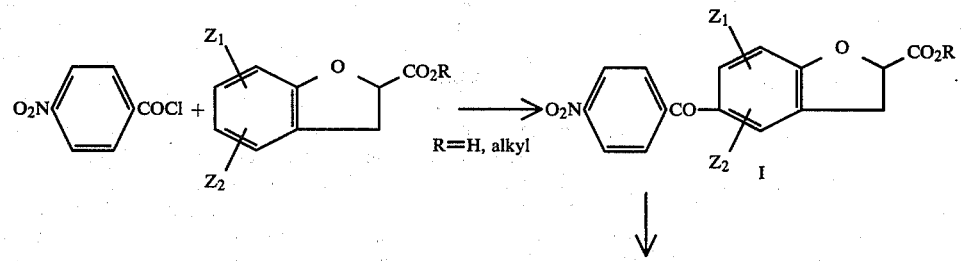

-continued
Reaction Scheme

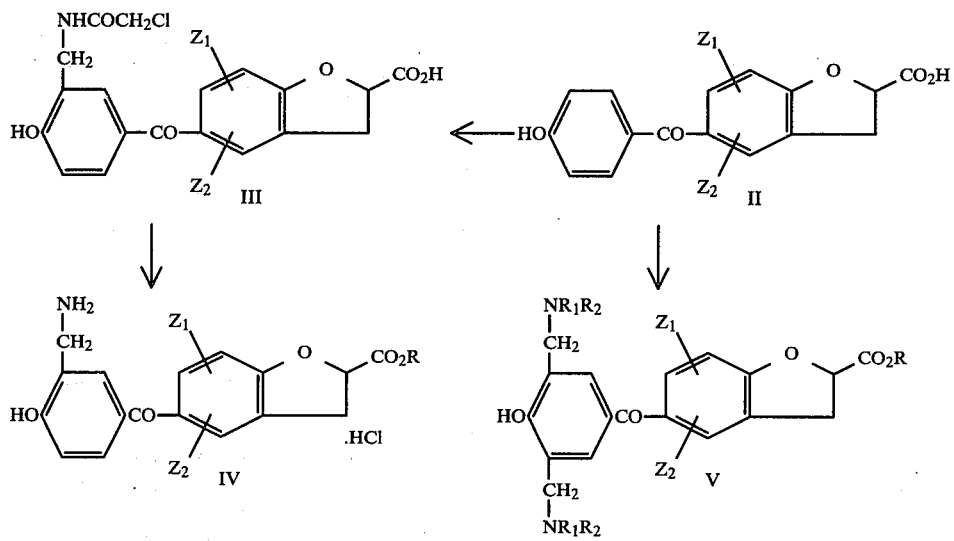

The compounds are synthesized by Friedel-Craft reaction of 4-nitrobenzoylchloride with substituted 2,3-dihydrobenzofuran-2-carboxylic acid or its ester with aluminum chloride to yield the condensed nitro derivatives (I), which are converted to the hydroxy derivatives (II) by acetaldoxime and sodium hydroxide in dimethylformamide at room temperature.

Amidoalkylation of the hydroxy derivatives (II) with 2-chloro-N-(hydroxymethyl)acetamide in methanesulfonic acid or concentrated sulfuric acid yield the chloroacetylaminomethyl derivatives (III) which are hydrolyzed by concentrated hydrochloric acid and ethanol to give the products (IV).

The Mannich bases (V) are obtained by heating the hydroxy derivatives (II) with excess amine and formaldehyde solution.

To prepare the diphenylmethane derivatives, the benzophenone compounds were allowed to react with sodium borohydride in trifluoroacetic acid. Elaboration of the reduced compounds to final product was effected by an analogous set of reactions as described above.

EXAMPLE 1

(±)
6,7-Dichloro-2,3-dihydro-5-(4-nitrobenzoyl)-2-benzofurancarboxylic acid

Anhydrous aluminum chloride (5.97 g., 0.0448 mole) was added in small portions to a stirred mixture of 2.6 g. (0.0112 mole) of 6,7-dichloro-2,3-dihydrobenzofuran-2-carboxylic acid and 6.24 g. (0.0336 mole) of 4-nitrobenzoyl chloride. The mixture was heated at 90° C. for 4 hours and then poured into 170 ml. of ice water and 10 ml. of concentrated hydrochloric acid. The product was extracted into ethyl acetate (200 ml.), washed with water, and then extracted with 5% aqueous sodium bicarbonate (100 ml.) from which the sodium salt of the product precipitated. The sodium salt of the product was filtered and transferred to a separatory funnel with 2 N hydrochloric acid (70 ml.) and ethyl acetate (150 ml.) and shaken until the solid dissolved. The ethyl acetate solution was washed with water, dried over sodium sulfate and evaporated in vacuo. The product was recrystallized from acetic acid; m.p. 243°–245°.

EXAMPLE 1a (±)
6,7-Dichloro-2,3-dihydro-5-(p-nitrobenzoyl)-benzofuran-2-carboxylic Acid A solution of ethyl 6,7-dichloro-2,3-dihydrobenzofuran-2-carboxylate (10.0 g.) and p-nitrobenzoyl chloride (14.2 g.) in methylene chloride (40 ml.) was placed on a cold water bath with mechanical agitation and treated with aluminum chloride (15.3 g.) portionwise over 5 minutes. The bath was then heated at 80°–90° C. for 1 hour and removed, and the mixture diluted with 100 ml. of methylene chloride.

The mixture was decomposed with 500 ml. of ice and 60 ml. of concentrated HCl and extracted into ether, then washed with aqueous saturated NaCl and evaporated to dryness. The residue was dissolved in 200 ml. EtOH, warmed to 60° C. with 200 ml. 1 N aqueous NaOH, and allowed to stir overnight.

The sodium salt was collected by filtration, distributed between ethyl acetate and diluted aqueous HCl, recovered from the organic phase as the acid by evaporation, recrystallized from acetonitrile with n-butyl chloride, and used without characterization. Yield was approximately 50%.

Calcd. for $C_{16}H_9Cl_2NO_6$: C, 50.28; H, 2.37; N, 3.67: Found: C, 49.99; H, 2.32; N, 3.57.

EXAMPLE 2

Ethyl (±)
6,7-Dichloro-2,3-dihydro-5-(4-hydroxybenzoyl)-2-benzofurancarboxylate 6,7-Dichloro-2,3-dihydro-5-(4-nitrobenzoyl)-2-benzofurancarboxylic acid (3.44 g., 0.009 mole) was added to a stirred mixture of 1.77 g. (0.03 mole) of acetaldoxime and 1.60 g. (0.04 mole) of crushed sodium hydroxide pellets in 25 ml. of dry dimethylformamide, cooled in an ice water bath. The mixture was stirred at room temperature overnight and poured into 60 ml. of water, acidified with concentrated hydrochloric acid and the product was extracted with ethyl acetate. The ethyl acetate solution was washed with water, dried over magnesium sulfate and evaporated in vacuo. The residue was recrystallized from diluted acetic acid; m.p. 192°–194° C.

Calcd. for $C_{16}H_{10}Cl_2O_5$: C, 54.41; H, 2.85: Found: C, 54.46; H, 3.01.

The solution of the product from above in 150 ml. of ethanol was treated with 0.5 ml. concentrated $H_2SO_4$ at reflux under a Soxhlet extractor containing 3A molecular sieves. After four hours, the ethanol was evaporated and replaced with ethyl acetate; washing with aqueous saturated NaCl, drying with $MgSO_4$, decolorization with charcoal, partial evaporation and recrystallization with hexanes provided the ethyl ester in quantitative yield.

EXAMPLE 3

(±) Ethyl 6,7-dichloro-2,3-dihydro-5-[(3-aminomethyl-4-hydroxy)benzoyl]-2-benzofurancarboxylate hydrochloride (A) and (±) Ethyl 6,7-dichloro-2,3-dihydro-5-{[(3,5-bis(aminomethyl)-4-hydroxy]benzoyl}-2-benzofurancarboxylate dihydrochloride (B)

2-Chloro-N-(hydroxymethyl)acetamide (0.69 g., 0.0056 mole) was added, in small portions, to a stirred solution of 1.41 g. (0.004 mole) of 6,7-dichloro-2,3-dihydro-5-(4-hydroxybenzoyl)-2-benzofurancarboxylic acid in 15 ml. of methanesulfonic acid. The mixture was stirred at room temperature for 5 hours and then poured into 500 ml. of ice water. The solid was filtered, washed with ice water, and dissolved in ethyl acetate. The ethyl acetate solution was washed twice with water, dried over sodium sulfate and evaporated in vacuo. To the residue was added 50 ml. of ethanol and 0.5 ml. of concentrated sulfuric acid and the mixture was stirred at room temperature overnight. The solution was evaporated in vacuo and the residue (ethyl esters) was taken up in ethyl acetate. The ethyl acetate solution was washed with aqueous sodium bicarbonate, water, and dried over sodium sulfate. After evaporation, the crude products were separated by chromatography over a silica gel 60 (70–230 mesh) column using a graded mixture of ethyl acetate and benzene into two pure fractions. The less polar fraction was refluxed with 30 ml. of ethanol and 10 ml. of concentrated hydrochloric acid for 8 hours. After evaporation, the residue was recrystallized from ethanol-ether to give product (A), m.p. 224°–227° C.

Calcd. for $C_{19}H_{17}Cl_2NO_5.HCl$: C, 51.08; H, 4.06; N, 3.14: Found: C, 50.95; H, 4.26; N, 3.12.

The more polar reaction was refluxed with 30 ml. of ethanol and 10 ml. of concentrated hydrochloride for 6 hours. After evaporation, the residue was recrystallized from ethanol-ether to yield product (B).

EXAMPLE 4

(±) Ethyl 6,7-dichloro-2,3-dihydro-5-[(3-chloro-4-hydroxy)benzoyl]-2-benzofurancarboxylate A mixture of 1.57 g. (0.0041 mole) of ethyl 6,7-dichloro-2,3-dihydro-5-(4-hydroxybenzoyl)-2-benzofurancarboxylate, 0.61 g. (0.0045 mole) of sulfuryl chloride, and 20 ml. of 1,2-dichloroethane was stirred and refluxed for 5 hours. After evaporation, the residue was triturated with ether, filtered, and recrystallized from toluene to yield the product, m.p. 168°–171° C.

EXAMPLE 5

(±) Ethyl 6,7-dichloro-2,3-dihydro-5-[(3-aminomethyl-5-chloro-4-hydroxy)-benzoyl]-2-benzofurancarboxylate hydrochloride 2-Chloro-N-(hydroxymethyl)acetamide (0.41 g., 0.0033 mole) was added to a stirred solution of 1.25 g. (0.003 mole) of ethyl 6,7-dichloro-2,3-dihydro-5-[(3-chloro-4-hydroxy)benzoyl]-2-benzofurancarboxylate in 5 ml. of methanesulfonic acid at 40° C. After the addition, the mixture was stirred and heated at 95° C. for 3¾ hours. On cooling, the mixture was poured into ice-water and the solid was filtered and washed thoroughly with ice water. The crude product was stirred and refluxed with 7 ml. of concentrated hydrochloric acid and 21 ml. of ethanol for 8 hours. After cooling, the solid was filtered and recrystallized from ethanol to yield the product, m.p. 237°–239° C.

Calcd. for $C_{19}H_{16}Cl_3NO_5.HCl.1/2H_2O$: C, 46.55; H, 3.70; N, 2.86: Found: C, 46.19; H, 3.45; N, 2.75.

EXAMPLE 6

(±) 6,7-Dichloro-2,3-dihydro-5-{[(3,5-bis(dimethylaminomethyl)-4-hydroxy]benzoyl}-2-benzofurancarboxylic acid 37% Formaldehyde solution (2.14 ml., 0.0285 mole) was added to a stirred solution of 4.27 ml. (0.094 mole) of 40% aqueous dimethylamine solution, cooled in an ice bath. After stirring at room temperature for ¼ hour, 1.77 g. (0.005 mole) of 6,7-dichloro-2,3-dihydro-5-(4-hydroxybenzoyl)-2-benzofurancarboxylic acid was added and the mixture was heated under gentle reflux for 20 hours. After evaporation, the residue was recrystallized from dimethylformamide to give the product, m.p. 220°(dec.).

EXAMPLE 7

(±) Ethyl 6,7-dichloro-2,3-dihydro-5-{[(3,5-bis(dimethylaminomethyl)-4-hydroxy]benzoyl}-2-benzofurancarboxylate dihydrochloride A mixture of 0.78 g. of 6,7-dichloro-2,3-dihydro-5-{[3,5-bis(dimethylaminomethyl)-4-hydroxy]benzoyl}-2-benzofurancarboxylic acid, 0.63 ml. of thionyl chloride and 16 ml. of ethanol was stirred and refluxed for 4 hours. After evaporation, the residue was recrystallized twice from ethanol-ether to yield the product, m.p. 173°–176°(dec.).

Calcd. for $C_{24}H_{28}Cl_2N_2O_5.2HCl.H_2O$: C, 49.16; H, 5.50; N, 4.78: Found: C, 48.85; H, 5.40; N, 4.81.

EXAMPLE 8

(±) Ethyl 6,7-dichloro-2,3-dihydro-5-[(3-benzyloxycarbonylaminomethyl-4-hydroxy)benzoyl]-2-benzofurancarboxylate A solution of 0.95 g. (0.0095 mole) of potassium bicarbonate in 10 ml. of water was added dropwise to a stirred mixture of 4.02 g. (0.0009 mole) of ethyl 6,7-dichloro-2,3-dihydro-5-[(3-aminomethyl-4-hydroxy)-benzoyl]-2-benzofurancarboxylate hydrochloride and 2.37 g. (0.0095 mole) of N-benzyloxycarbonyloxysuccinimide in 40 ml. of acetonitrile, cooled in an ice water bath. After the addition, the mixture was stirred at room temperature for 1¾ hours. The organic layer was separated and evaporated in vacuo to dryness. The residue was dissolved in methylene chloride, washed with 5% aqueous potassium bicarbonate, brine, 1 N hydrochloric acid, brine, and dried over anhydrous sodium sulfate. After evaporation, the product was obtained by triturating the residue with ethylacetate and hexane, m.p. 150°–154° C.

EXAMPLE 9

(±) 6,7-Dichloro-2,3-dihydro-5-[(3-benzyloxycarbonylaminomethyl-4-hydroxy)benzoyl]-2-benzofurancarboxamide Ammonia gas was passed through a stirred solution of 1.09 g. (0.002 mole) of ethyl 6,7-dichloro-2,3-dihydro-5-[(3-benzyloxycarbonylaminomethyl-4-hydroxy)benzoyl]-2-benzofurancarboxylate in 150 ml. of ethanol for 3 hours. After stirring at room temperature overnight, the mixture was evaporated in vacuo to dryness. The residue was triturated with 1 N hydrochloric acid and methylene chloride, filtered, and recrystallized from ethanol to give the product, m.p. 133°–137° C.

EXAMPLE 10

(±) 6,7-Dichloro-2,3-dihydro-5-[(3-aminomethyl-4-hydroxy)benzoyl]-2-benzofurancarboxamide hydrochloride A mixture of 0.87 g. (0.0017 mole) of 6,7-dichloro-2,3-dihydro-5-[(3-benzyloxycarbonylaminomethyl-4-hydroxy)benzoyl]-2-benzofurancarboxamide, 0.09 g. of 5% palladium-on-carbon and 0.6 ml. of concentrated hydrochloric acid in 100 ml. of methyl cellosolve was hydrogenated under 3 atmospheric pressure at room temperature for 3 hours. After removing the catalyst, the solution was evaporated in vacuo to dryness and the residue was recrystallized from ethanol-ether to yield the product, m.p. >250° C.

Calcd. for $C_{17}H_{14}Cl_2N_2O_4 \cdot HCl$: C, 48.88; H, 3.62; N, 6.71: Found: C, 48.45; H, 3.74; N, 6.44.

EXAMPLE 11

(±) 6,7-Dichloro-2,3-dihydro-5-[(3-benzyloxycarbonylaminomethyl-4-hydroxy)benzoyl]-2-(hydroxymethyl)benzofuran (A)

and (±) 6,7-Dichloro-2,3-dihydro-5-[(3-benzyloxycarbonylaminomethyl-4-hydroxy)-α-hydroxybenzyl]-2-(hydroxymethyl)benzofuran (B)

Sodium borohydride (1.6 g., 0.0423 mole) was added to a solution of 3.0 g. (0.0055 mole) of ethyl 6,7-dichloro-2,3-dihydro-5-[(3-benzyloxycarbonylaminomethyl-4-hydroxy)benzoyl]-2-benzofurancarboxylate in 150 ml. of ethanol, cooled in an ice water bath at 5°–10°. The mixture was stirred at 5°–10° for 2½ hours and evaporated in vacuo. The residue was triturated with water, acidified with aqueous citric acid, and extracted with methylene chloride. The methylene chloride solution was washed with brine, dried over anhydrous sodium sulfate, and evaporated in vacuo. The residue was purified by high pressure liquid chromatography using silica gel column and 1,2-dichloroethane (98.9)-ethanol (1.1) to give products (A) and (B).

EXAMPLE 12

(±) 6,7-Dichloro-2,3-dihydro-5-[(3-aminomethyl-4-hydroxy)benzoyl]-2-(hydroxymethyl)benzofuran hydrochloride A solution of 1.49 g. of 6,7-dichloro-2,3-dihydro-5-[(3-benzyloxycarbonylaminomethyl-4-hydroxy)benzoyl]-2-(hydroxymethyl)benzofuran, 0.15 g. of 5% Pd on carbon, 0.4 ml. of hydrochloric acid, and 100 ml. of ethanol was hydrogenated for one hour. After removal of the catalyst, the solution was evaporated in vacuo to dryness and the residue was recrystallized from ethanol-ether to yield the product, m.p. 248°–250° C.

Calcd. for $C_{17}H_{15}Cl_2NO_4 \cdot HCl$: C, 50.45; H, 3.99; N, 3.46: Found: C, 50.13; H, 4.34; N, 3.27.

EXAMPLE 13

(±) Ethyl 6,7-dichloro-2,3-dihydrobenzofuran-2-carboxylate

A solution of 50 g. of crude 6,7-dichloro-2,3-dihydrobenzofuran-2-carboxylic acid in 500 ml. absolute ethanol was treated with 3 ml. concentrated $H_2SO_4$ at reflux for 5 hours under a Soxhlet extractor containing 3A molecular sieves. The solution was then evaporated to dryness, redissolved in ethyl acetate, and washed with agueous saturated NaCl, aqueous saturated NaHCO₃, and again aqueous saturated NaCl.

The ethyl acetate solution was dried (MgSO₄), decolorized (charcoal) and evaporated to an oily residue. Fractional recrystallization from methylene chloride with hexane gave first a fluffy brown impurity and then 33.4 g. (59.62%) of the product, large white crystals, m.p. 75°–76° C.

Calcd. for $C_{11}H_{10}Cl_2O_3$: C, 50.06; H, 3.86: Found: C, 50.29; H, 3.79.

EXAMPLE 14

(±) Ethyl 6,7-dichloro-2,3-dihydro-5-(p-hydroxybenzyl)-benzofuran-2-carboxylate

To trifluoroacetic acid (120 ml.) under a nitrogen atmosphere were added sodium borohydride pellets (5.39 g.) over a period of 30 minutes at 5° C. A solution of ethyl 6,7-dichloro-2,3-dihydro-5-(p-hydroxybenzoyl)-benzofuran-2-carboxylate (7.35 g.) in methylene chloride (50 ml.) was then added dropwise over 30 minutes, and the mixture stirred at room temperature for 22 hours.

The mixture was diluted with 300 ml. of $H_2O$, extracted into methylene chloride and washed copiously with aqueous saturated NaCl. The extract was dried (MgSO₄), decolorized and evaporated to yield 5.70 g. of an oil which began to crystallize on standing for 48 hours. Recrystallization from chloroform with hexane afforded 4.67 g. (65.96%) of white crystals, m.p. 104°–105° C.

Calcd. for $C_{18}H_{16}Cl_2O_4$: C, 58.87; H, 4.39; O, 17.43: Found: C, 58.69; H, 4.57; O, 16.89.

EXAMPLE 15

(±) 6,7-2,3-Dihyrdo-5-(p-hydroxybenzyl)-benzofuran-2-carboxylic Acid 250 mg. of the above ethyl ester was dissolved in 5 ml. EtOH and treated dropwise with 25 ml. of 2 N aqueous NaOH. After 30 minutes, the mixture was partially evaporated and diluted with 10 ml. of H$_2$O, then acidified with concentrated HCl to yield a white precipitate, 220 mg., m.p. 232°–235° C.

Calcd. for C$_{16}$H$_{12}$Cl$_2$O$_4$: C, 56.66; H, 3.56; O, 18.86: Found: C, 56.10; H, 3.62; O, 18.23.

EXAMPLE 16

(±)
Ethyl-5-(3-chloroacetamideomethyl-4-hydroxybenzyl)-6,7-dichloro-2,3-dihydrobenzofuran-2-carboxylate Ethyl 6,7-dichloro-2,3-dihydro-5-(p-hydroxybenzyl)-benzofuran-2-carboxylate (4.12 g.) was dissolved in 36 ml. of glacial acetic acid with gentle heating; the solution was cooled on an ice bath and concentrated H$_2$SO$_4$ (4 ml.) was added, followed by portionwise addition of N-hydroxymethyl-2-chloroacetamide (1.41 g.). The mixture was allowed to stir at room temperature for 20 hours, then decanted slowly into ice water with vigorous agitation.

Extraction into ethyl acetate, washing (aqueous saturated NaCl), drying (MgSO$_4$), and evaporation yielded an oil, which was dissolved in 150 ml. of EtOH and treated with 0.5 ml. of H$_2$SO$_4$ at room temperature for 18 hours. The ethanol was partially evaporated under vacuum and the residue distributed between ethyl acetate and aqueous saturated NaCl. The organic layer was washed with aqueous saturated NaCl, dried over MgSO$_4$, and evaporated to yield a gum.

The crude ethyl ester was chromatographed on a silica gel column using benzene/ethyl acetate in a step gradient from 3:1 to 2:1. Evaporation yielded 2.41 g. of white crystals, m.p. 185°–187° C.

Calcd. for C$_{21}$H$_{20}$Cl$_3$NO$_5$: C, 53.35; H, 4.26; N, 2.96: Found: C, 53.64; H, 4.32; N, 2.93.

EXAMPLE 17

(±)
Ethyl-5-(3,5-bis-chloroacetamidomethyl-4-hydroxybenzyl)-6,7-dichloro-2,3-dihydrobenzofuran-2-carboxylate A major chromatographically isolated by-product of the above production of ethyl 5-(3-chloroacetamidomethyl-4-hydroxybenzyl)-6,7-dichloro-2,3-dihydrobenzofuran-2-carboxylate was collected, evaporated to dryness and recrystallized from chloroform/hexane to yield 480 mg. of pale yellow amorphous solid, m.p. 156°–160° C.

Calcd. for C$_{24}$H$_{24}$Cl$_4$NO$_6$: C, 49.85; H, 4.18; N, 4.84: Found: C, 50.09; H, 4.22; N, 4.80.

EXAMPLE 18

(±)
5-(3-Chloroacetamidomethyl-4-hydroxybenzyl)-6,7-dichloro-2,3-dihydro-2-hydroxymethylbenzofuran The mono-amidoalkylated product of Example 16 (700 mg.) was dissolved in absolute ethanol (50 ml.) and stirred under a nitrogen atmosphere. Powdered sodium borohydride was added portionwise over one hour. After 21 hours the residue was partitioned between ethyl acetate and aqueous extracted NaCl, and the organic phrase was collected. Washing with additional aqueous saturated NaCl and evaporation produced the crude alcohol as a glass; this material was chromatographed on a silica gel column using benzene/ethyl acetate, 9:1, as eluent. Evaporation afforded a colorless glass (510 mg., 80.34%) which was used as such in the next step.

EXAMPLE 19

(±)
5-(3-Aminomethyl-4-hydroxybenzyl)-6,7-dichloro-2,3-dihydro-2-hydroxymethylbenzofuran hydrochloride The glass from Example 18 (500 mg.) was dissolved in ethanol (20 ml.) and treated with 3 N aqueous HCl (100 ml.) at reflux for four hours. The resulting solution was partially evaporated and chilled on an ice bath to yield a white crystalline precipitate (400 mg., 87.78%), m.p. 227°–230° (dec.).

Calcd. for C$_{17}$H$_{18}$Cl$_3$NO$_3$.1/3H$_2$O: C, 51.47; H, 4.74; N, 3.53: Found: C, 51.49; H, 4.55; N, 3.57.

EXAMPLE 20

(±) Ethyl 5-[3,5-bis-(aminomethyl)-4-hydroxybenzyl]-6,7-dichloro-2,3-dihydrobenzofuran-2-carboxylate dihydrochloride The bis-amidoalkylated material from Example 17 (430 mg.) was dissolved in 20 ml. of ethanol and treated with 5 ml. of concentrated HCl at reflux for 4 hours. The mixture was then evaporated to near dryness and redissolved in ethanol through six repetitions. Complete drying in vacuo afforded a beige crystalline solid (330 mg., 89.07%); m.p. 215°–219° C. (dec.)

Calcd. for C$_{20}$H$_{24}$Cl$_4$N$_2$O$_4$.1/2H$_2$O: C, 47.36; H, 4.97; N, 5.52: Found: C, 47.20; H, 4.75; N, 5.52.

EXAMPLE 21

(±) Ethyl 5-(3-aminomethyl-4-hydroxybenzyl)-6,7-dichloro-2,3-dihydrobenzofuran-2-carboxylate hydrochloride The mono-amidoalkylated compound from Example 16 above (1.71 g.) was processed as per Example 20 above to yield 1.40 g. (89.00%) of off-white crystals; m.p. 227°–220° C. (dec.)

Calcd. for C$_{19}$H$_{20}$Cl$_3$NO$_4$.1/4H$_2$O: C, 52.19; H, 4.73; N, 3.20: Found: C, 52.01; H, 4.61; N, 3.24.

EXAMPLE 22

(±)
5-(3-Aminomethyl-4-hydroxybenzyl)-6,7-dichloro-2,3-dihydrobenzofuran-2-carboxylic acid hydrochloride The ethyl ester from Example 21 (400 mg.) was suspended in 100 ml. 3 N of aqueous HCl and refluxed for four hours. The resulting solution was evaporated to dryness and resuspended in H$_2$O three times to yield 330 mg. of light beige crystalline solid, m.p. 255°–259° C. (dec.)

Calcd. for C$_{17}$H$_{16}$Cl$_3$NO$_4$.1/4H$_2$O: C, 49.90; H, 4.06; N, 3.42: Found: C, 49.87; H, 3.84; N, 3.46.

EXAMPLE 23

(±)-5-(3-Benzyloxycarboxamidomethyl-4-hydroxybenzyl)-6,7-dichloro-2,3-dihydrobenzofuran-2-carboxamide The ethyl ester from Example 21 (660 mg.) and N-benzyloxycarbonyloxysuccinimide (400 mg.) were dissolved in 15 ml. of 80% aqueous ethanol and cooled on an ice bath. A solution of potassium bicarbonate (160 mg.) in H$_2$O (1½ ml.) was then added dropwise with stirring. A precipitate formed which was dissolved in an additional portion of ethanol (5 ml.). After being stirred at ambient temperature overnight, the resulting solution was evaporated and the residue dissolved in methylene chloride. Washing with aqueous saturated NaHCO$_3$ and aqueous saturated NaCl, drying (MgSO$_4$), and evaporation yielded the CBZ-derivative, an oil which was used without characterization.

The entire sample was dissolved in absolute ethanol and sparged vigorously with anhydrous ammonia for three hours, during which time ice bath cooling was applied. After standing overnight at room temperature, the ethanol was evaporated and the residue dissolved in methyl cellosolve. Acidification with concentrated HCl followed by decantation into excess cold H$_2$O yielded the product.

EXAMPLE 24

(±)

5-(3-Aminomethyl-4-hydroxybenzyl)-6,7-dichloro-2,3-dihydrobenzofuran-2-carboxamide hydrochloride The CBZ-carboxamide from Example 23 was hydrogenated with 5% palladium-on-carbon according to Example 10 to yield the product.

EXAMPLE 25

(±)

5-(3'-Aminomethyl-4-hydroxybenzoyl)-6,7-dichloro-2,3-dihydrobenzofuran-2-carboxylic acid hydrochloride A sample of crude ethyl 5-(3-aminomethyl-4-hydroxybenzoyl)-6,7-dichloro-2,3-dihydrobenzofuran-2-carboxylate (600 mg.) was dissolved in 10 ml. of ethanol and treated with 4% aqueous HCl (125 ml.) for five hours at reflux.

The solution was filtered while still warm to remove traces of carbon and impurities, evaporated to dryness, and the off-white crystalline product dried for 48 hours in vacuo; m.p. 230°–235° C. (dec.).

Calcd. for C$_{17}$H$_{14}$Cl$_3$NO$_5$.H$_2$O: C, 46.76; H, 3.69; N, 3.21: Found: C, 46.55; H, 3.27; N, 3.23.

Diuretic Screening of the compounds of this invention was conducted in normotensive rats using the following procedure.

Female rats (Sprague-Dawley), weighing 175–225 grams, are placed on a diet of sucrose and water overnight. DOCA (deoxycorticosterone acetate), is prepared as a 2.5% suspension in 0.2% hydroxypropyl methylcellulose. Each rat is administered 0.2 ml. subcutaneously of the DOCA suspension 2 hours prior to treatment with the test compound.

The suspension or solutions of test compounds are prepared daily. The compounds are suspended in 0.2% hydroxypropyl methylcellulose (vehicle) and administered orally (by gavage) in 2 ml./kg of the rat's body weight. Immediately after dosing, each rat is loaded with an isotonic mixture of NaCl and KCl in the ratio of 40:60 equivalent to 3% of the rat's body weight.

The rats are placed in individual stainless steel metabolism cages. No food or water is allowed during the experiment. Urine is collected for a 4 hour period. The volume of urine is measured at 4 hours and an aliquot is taken for analysis of urine sodium and potassium concentrations. Sodium and potassium are measured using an Instrumentation Labs Digital Flame Photometer. The data are reported in: volume ml.; sodium and potassium-meq./l.

Standard screening procedures involves the testing of 2 doses of each compound using 2 rats per dose in a 2-stage screening system. The normal screening doses are 30 and 100 mg./kg. orally. Urinary excretions of sodium and potassium are expressed as meq./kg. of the rat's body weight.

TABLE I

| Compound* Example | R$_1$ | R$_2$ | X | A | Z$_1$ | Z$_2$ | W | ED$_2$ |
|---|---|---|---|---|---|---|---|---|
| 3A | H | H | H | CO | Cl | Cl | CO$_2$C$_2$H$_5$ | 0.12 |
| 5 | H | H | Cl | CO | Cl | Cl | CO$_2$C$_2$H$_5$ | 21.5 |
| 7 | CH$_3$ | CH$_3$ | CH$_2$N(CH$_3$)$_2$ | CO | Cl | Cl | CO$_2$C$_2$H$_5$ | 1.82 |
| 10 | H | H | H | CO | Cl | Cl | CONH$_2$ | 2.95 |
| 12 | H | H | H | CO | Cl | Cl | CH$_2$OH | 0.95 |
| 19 | H | H | H | CH$_2$ | Cl | Cl | CH$_2$OH | 10.2 |
| 20 | H | H | CH$_2$NH$_2$ | CH$_2$ | Cl | Cl | CO$_2$C$_2$H$_5$ | 49.0 |
| 21 | H | H | H | CH$_2$ | Cl | Cl | CO$_2$C$_2$H$_5$ | 8.0 |

*as HCl salt

What is claimed is:

1. A compound of the formula

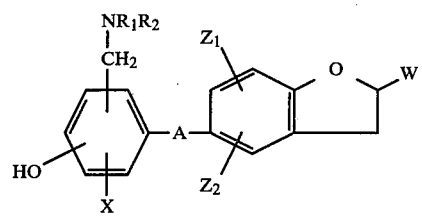

wherein R$_1$ and R$_2$ independently of one another denote hydrogen or loweralkyl; A is CO, CH$_2$, O, S, SO or CHOH; X is hydrogen, halo, loweralkyl, or —CH$_2$NR$_1$R$_2$ wherein R$_1$ and R$_2$ are as defined above; W is COOR wherein R is hydrogen or alkyl of 1–10 carbon atoms, CH$_2$OH, CONR$_1$R$_2$ or CH$_2$NR$_1$R$_2$ wherein R$_1$ and R$_2$ are as defined above; and Z$_1$ and Z$_2$ independently of one another denote hydrogen, halo or loweralkyl; and pharmaceutically acceptable salts thereof.

2. The compound of claim 1 wherein R$_1$ and R$_2$ independently of one another denote hydrogen or loweralkyl, A is CO or CH$_2$, X is hydrogen, chloro, CH$_2$NH$_2$ or CH$_2$N(CH$_3$)$_2$, W is COOR wherein R is loweralkyl, CH$_2$OH or CONH$_2$, and Z$_1$ and Z$_2$ are chloro.

3. A compound of claim 1 wherein R$_1$ and R$_2$ independently of one another denote hydrogen or CH$_3$, and W is —CO$_2$C$_2$H$_5$, —CH$_2$OH or —CONH$_2$.

4. A compound of claim 3 wherein R$_1$ and R$_2$ are hydrogen, X is hydrogen, A is CO, Z$_1$ and Z$_2$ are chloro, and W is —CO$_2$C$_2$H$_5$.

5. A compound of claim 3 wherein R$_1$ and R$_2$ are hydrogen, X is chloro, A is —CO, Z$_1$ and Z$_2$ are chloro, and W is —CO$_2$C$_2$H$_5$.

6. A compound of claim 3 wherein $R_1$ and $R_2$ are —$CH_3$, X is —$CH_2N(CH_3)_2$, A is —CO, $Z_1$ and $Z_2$ are chloro, and W is —$CO_2C_2H_5$.

7. A compound of claim 3 wherein $R_1$ and $R_2$ are hydrogen, X is hydrogen, A is —CO, $Z_1$ and $Z_2$ are chloro, and W is —$CONH_2$.

8. A compound of claim 3 wherein $R_1$ and $R_2$ are hydrogen, X is hydrogen, A is —CO, $Z_1$ and $Z_2$ are chloro, and W is —$CH_2OH$.

9. A compound of claim 3 wherein $R_1$ and $R_2$ are hydrogen, X is hydrogen, A is —$CH_2$, $Z_1$ and $Z_2$ ae chloro, and W is —$CH_2OH$.

10. A compound of claim 3 wherein $R_1$ and $R_2$ are hydrogen, X is —$CH_2NH_2$, A is —$CH_2$, Z, and $Z_2$ are chloro, and W is —$CO_2C_2H_5$.

11. A compound of claim 3 wherein $R_1$ and $R_2$ are hydrogen, X is hydrogen, A is —$CH_2$, $Z_1$ and $Z_2$ are chloro, and W is —$CO_2C_2H_5$.

12. A pharmaceutical composition useful as a diuretic which comprises a therapeutically effective amount of a compound of the formula

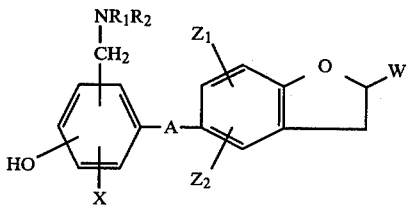

wherein $R_1$ and $R_2$ independently of one another denote hydrogen or loweralkyl; A is CO, $CH_2$, O, S, SO or CHOH; X is hydrogen, halo, loweralkyl, or —$CH_2NR_1R_2$ wherein $R_1$ and $R_2$ are as defined above; W is COOR wherein R is hydrogen or alkyl of 1–10 carbon atoms, $CH_2OH$, $CONR_1R_2$ or $CH_2NR_1R_2$ wherein $R_1$ and $R_2$ are as defined above; and $Z_1$ and $Z_2$ independently of one another denote hydrogen, halo or loweralkyl; and pharmaceutically acceptable salts thereof, and a pharmaceutically acceptable carrier.

13. The compound of claim 12 wherein $R_1$ and $R_2$ independently of one another denote hydrogen or loweralkyl, A is CO or $CH_2$, X is hydrogen, chloro, $CH_2NH_2$ or $CH_2N(CH_3)_2$, W is COOR wherein R is loweralkyl, $CH_2OH$ or $CONH_2$, and $Z_1$ and $Z_2$ are chloro.

14. The composition of claim 13 wherein $R_1$ and $R_2$ independently of one another denote hydrogen or $CH_3$, and W is —$CO_2C_2H_5$, —$CH_2OH$ or —$CONH_2$.

15. The composition of claim 13 wherein $R_1$ and $R_2$ are hydrogen, X is hydrogen, A is CO, $Z_1$ and $Z_2$ are chloro, and W is —$CO_2C_2H_5$.

16. The composition of claim 13 wherein $R_1$ and $R_2$ are hydrogen, X is chloro, A is —CO, $Z_1$ and $Z_2$ are chloro, and W is —$CO_2C_2H_5$.

17. The composition of claim 13 wherein $R_1$ and $R_2$ are —$CH_3$, X is —$CH_2N(CH_3)_2$, A is —CO, $Z_1$ and $Z_2$ are chloro, and W is —$CO_2C_2H_5$.

18. The composition of claim 13 wherein $R_1$ and $R_2$ are hydrogen, X is hydrogen, A is —CO, $Z_1$ and $Z_2$ are chloro, and W is —$CONH_2$.

19. The composition of claim 13 wherein $R_1$ and $R_2$ are hydrogen, W is hydrogen, A is —CO, $Z_1$ and $Z_2$ are chloro, and W is —$CH_2OH$.

20. The composition of claim 13 wherein $R_1$ and $R_2$ are hydrogen, X is hydrogen, A is —$CH_2$, $Z_1$ and $Z_2$ are chloro, and W is —$CH_2OH$.

21. The composition of claim 13 wherein $R_1$ and $R_2$ are hydrogen, X is hydrogen, A is —$CH_2$, $Z_1$ and $Z_2$ are chloro, and W is —$CO_2C_2H_5$.

22. A method of increasing the urinary excretion of a patient comprising administering to a patient in need of such treatment a therapeutically effective amount of a diuretic agent of the formula

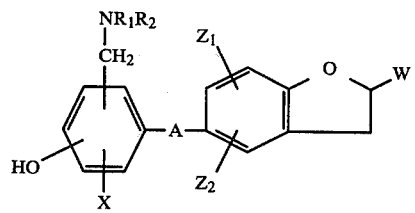

wherein $R_1$ and $R_2$ independently of one another denote hydrogen or loweralkyl; A is CO, $CH_2$, O, S, SO or CHOH; X is hydrogen, halo, loweralkyl, or —$CH_2NR_1R_2$ wherein $R_1$ and $R_2$ are as defined above; W is COOR wherein R is hydrogen or alkyl of 1–10 carbon atoms, $CH_2OH$, $CONR_1R_2$ or $CH_2NR_1R_2$ wherein $R_1$ and $R_2$ are as defined above; and $Z_1$ and $Z_2$ independently of one another denote hydrogen, halo or loweralkyl; and pharmaceutically acceptable salts thereof.

23. The method of claim 22 wherein $R_1$ and $R_2$ independently of one another denote hydrogen or loweralkyl, A is CO or $CH_2$, X is hydrogen, chloro, $CH_2NH_2$ or $CH_2N(CH_3)_2$, W is COOR wherein R is loweralkyl, $CH_2OH$ or $CONH_2$, and $Z_1$ and $Z_2$ are chloro.

24. The method of claim 22 wherein $R_1$ and $R_2$ independently of one another denote hydrogen or $CH_3$, and W is —$CO_2C_2H_5$, —$CH_2OH$ or —$CONH_2$.

25. The method of claim 24 wherein $R_1$ and $R_2$ are hydrogen, X is hydrogen, A is CO, $Z_1$ and $Z_2$ are chloro, and W is —$CO_2C_2H_5$.

26. The method of claim 24 wherein $R_1$ and $R_2$ are hydrogen, X is chloro, A is —CO, $Z_1$ and $Z_2$ are chloro, and W is —$CO_2C_2H_5$.

27. The method of claim 24 wherein $R_1$ and $R_2$ are —$CH_3$, X is —$CH_2N(CH_3)_2$, A is —CO, $Z_1$ and $Z_2$ are chloro, and W is —$CO_2C_2H_5$.

28. The method of claim 24 wherein $R_1$ and $R_2$ are hydrogen, X is hydrogen, A is —CO, $Z_1$ and $Z_2$ are chloro, and W is —$CONH_2$.

29. The method of claim 24 wherein $R_1$ and $R_2$ are hydrogen, X is hydrogen, A is —CO, $Z_1$ and $Z_2$ are chloro, and W is —$CH_2OH$.

30. The method of claim 24 wherein $R_1$ and $R_2$ are hydrogen, X is hydrogen, A is —$CH_2$, $Z_1$ and $Z_2$ ae chloro, and W is —$CH_2OH$.

31. The method of claim 24 wherein $R_1$ and $R_2$ are hydrogen, X is —$CH_2NH_2$, A is —$CH_2$, $Z_1$ and $Z_2$ are chloro, and W is —$CO_2C_2H_5$.

* * * * *